United States Patent [19]

Hesson

[11] Patent Number: 4,639,454
[45] Date of Patent: Jan. 27, 1987

[54] PHENYLQUINAZOLINECARBOXYLIC ACIDS AND DERIVATIVES AS CANCER CHEMOTHERAPEUTIC AGENTS

[75] Inventor: David P. Hesson, Wilmington, Del.

[73] Assignee: E. I. Du Pont de Nemours and Company, Wilmington, Del.

[21] Appl. No.: 692,412

[22] Filed: Jan. 17, 1985

[51] Int. Cl.$^4$ .................. A61K 31/505; C07D 239/74
[52] U.S. Cl. ...................................... 514/259; 544/283
[58] Field of Search ........................ 544/283; 514/259

[56] References Cited

U.S. PATENT DOCUMENTS

| | | | |
|---|---|---|---|
| 3,135,659 | 6/1964 | Shetty et al. | 544/290 |
| 3,169,129 | 2/1965 | Rodgers et al. | 544/283 |
| 3,215,694 | 11/1965 | Rachlin et al. | 544/283 |
| 3,637,693 | 1/1972 | Otterstedt et al. | 544/283 |
| 3,772,274 | 11/1973 | Kaplan | 544/283 |
| 3,819,628 | 6/1974 | Simpson | 544/293 |
| 3,843,652 | 10/1974 | Findeisen et al. | 544/283 |
| 3,998,951 | 12/1976 | Harnish et al. | 544/283 |
| 4,159,330 | 6/1979 | Doria et al. | 544/289 |
| 4,435,003 | 3/1984 | Fletcher | 544/282 |

FOREIGN PATENT DOCUMENTS

112776AZ  7/1984  European Pat. Off. .

OTHER PUBLICATIONS

Meyer, "Chemical Abstracts", vol. 65, 1966, Col. 16968e.
Pater, "Chemical Abstracts", vol. 74, 1971, Col. 12455t.
Bullock, et al., "Chemical Abstracts", vol. 74, 1971, Col. 31687m.
Glukhovets, et al., "Chemical Abstracts", vol. 78, 1973, Col. 97588u.
Smith, et al., "Chemical Abstracts", vol. 83, 1975, Col. 113168t.
Smith, et al., "Chemical Abstracts", vol. 84, 1976, Col. 84:90102w.
Cornforth, "Chemical Abstracts", vol. 86, 1977, Col. 86:13997p.
Yao, et al., "Chemical Abstracts", vol. 101, 1984, Col. 101:151810u.
A. Bischler and H. P. Muntendah [*Ber.*, 28. 723 (1895)] and M. T. Bogert and F. P. Nabenhauer [*J. Am. Chem. Soc.*, 46, 1702, (1924)].
Meerwein, et al., [*Chem. Ber.*, 89, 224 (1956)].
R. Pater, [*J. Heterocycl. Chem.*, 7(5), 1113–1124, 1970].
W. Yao, et al., *Yaoxue Xuebao*, 19 (1), 76–78 (1984) (Chinese).
G. G. Glukhovets and B. I. Ardashev, *Zh. Khim.*, 1972, Abstract No. 17Zh309 (Russian).
G. J. Stefanovic, et al., [*Recueil,* 80, 149–157 (1961)].

*Primary Examiner*—Glennon H. Hollrah
*Assistant Examiner*—James H. Turnipseed

[57] ABSTRACT

Phenylquinazolinecarboxylic acids and derivatives thereof, such as 2-(1,1'-biphenyl-4-yl)-6-fluoro-4-quinazoline carboxylic acid, sodium salt and 2-(1,1'-biphenyl-4-yl)-4-quinazoline carboxylic acid, sodium salt, are useful as tumor-inhibiting agents.

21 Claims, No Drawings

PHENYLQUINAZOLINECARBOXYLIC ACIDS AND DERIVATIVES AS CANCER CHEMOTHERAPEUTIC AGENTS

BACKGROUND OF THE INVENTION

1. Field of the Invention

This invention relates to quinazoline-4-carboxylic acids, processes for preparing them, pharmaceutical compositions containing them and methods of using them as cancer chemotherapeutic agents.

2. Literature Background

Only a small number of 2-aryl-quinazoline-4-carboxylic acids are known. Most have been prepared via a Bischler Synthesis which entails condensation of ammonia with an appropriate N-acylated isatinic acid.

A. Bischler and H. P. Muntendam [Ber., 28. 723 (1895)] and M. T. Bogert and F. P. Nabenhauer [J. Am. Chem. Soc., 46, 1702, (1924)] report 2-aryl-quinazoline-4-carboxylic acids, prepared by the Bischler Synthesis, having the formula:

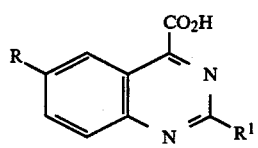

where

R=H or $CH_3$; and
$R^2$=$CH_3$, $C_2H_5$, $C_6H_5$ or $C_6H_4CO_2H$.

Meerwein, et al., [Chem. Ber., 89, 224 (1956)] report the synthesis of 2-phenyl-4-quinazoline carboxylic acid from reaction of N-phenylbenzimidoyl chloride and ethylcyanoformate in o-dichlorobenzene containing stannic chloride.

W. Yao, et al. [Yaoxue Xuebao, 19 (1), 76–78 (1984)] report antimalarial quinazoline-4-methanols derived from the corresponding acids including 2-phenyl-4-quinazoline carboxylic acid.

G. G. Glukhovets and B. I. Ardashev [Zh. Khim. 1972, Abstract No. 17Zh309] describe quinazoline analogs of cinchophen of the formula:

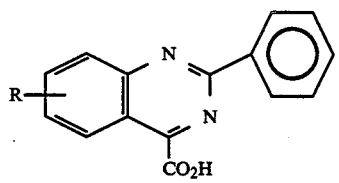

where R is 4-methyl, 7-methyl or 8-methyl.

R. Pater [J. Heterocycl. Chem., 7(5), 1113–1124, 1970] reports 2-(o-hydroxyphenyl)-4-quinazolinecarboxylic acid, prepared via Bischler's Synthesis as an intermediate to photostable o-hydroxyphenylquinazolines.

M. C. Dubroeucq, et al., in European Patent Appln. No. 112776AZ report 2-(2-chlorophenyl)-4-quinazolinecarboxylic acid which was prepared as an intermediate to the corresponding carboxamide of the formula:

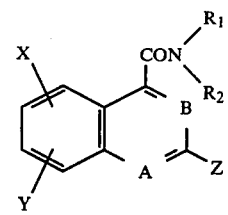

where

A and B are independently N or CH;
Z can be phenyl or substituted phenyl; and
X and Y are H, halogen, alkyl of 1–3 carbons, alkoxy of 1–3 carbons, nitro, or $CF_3$.

These compounds are useful as anxiolytics, antihypertensives, anti-epileptics and anti-angina agents.

Japanese Patent No. J58172-379-A issued Feb. 4, 1982 describes quinazoline derivatives, which are useful as vasodilators and blood flow improving drugs, of the formula:

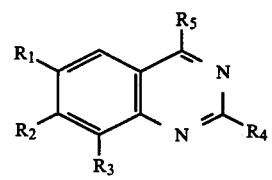

where $R_1$ and $R_3$ are lower alkyl;
$R_2$ is optionally branched carbonyl;
$R_4$ can be phenyl; and
$R_5$ is amongst others, alkoxy, dialkylaminoalkoxy, 1-piperidinoalkoxy, and alkylamino.

Hesson, in copending U.S. patent application Ser. No. 605,104, filed Apr. 4, 1984 describes pharmaceutical compositions, and their method of use as antitumor agents or phenylquinolinecarboxylic acids and derivatives of the formula:

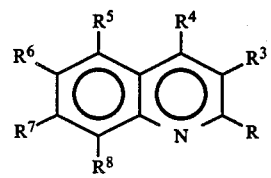

wherein
R is

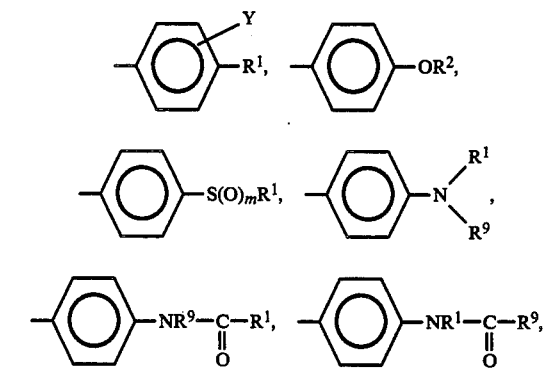

-continued

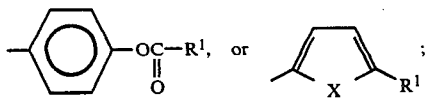

X is O, S(O)$_q$, NH or CH=N;
R$^1$ is CH$_3$CH$_2$(CH$_3$)CH, alkyl of 5–12 carbon atoms, alkenyl of 5–12 carbon atoms, cycloalkyl of 3–7 carbon atoms, cycloalkylalkyl of 5–12 carbon atoms, cycloalkenyl of 5–7 carbon atoms,

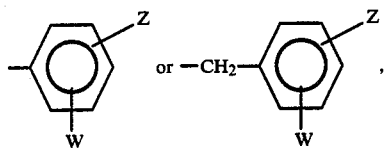

when R is

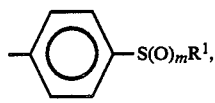

R$^1$ can be in addition alkyl of 3–4 carbon atoms;
R$^2$ is

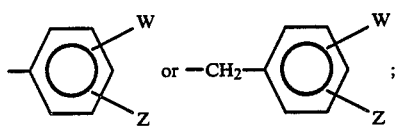

R$^3$ is H, alkoxy of 1–3 carbon atoms, alkylthio of 1–3 carbon atoms or alkyl of 1–3 carbon atoms optionally substituted with one or more of F, Cl, Br or (CH$_2$)$_p$COR$^{10}$ where p is 1, 2, 3 or 4;
R$^4$ is CO$_2$H or CO$_2$R$^{11}$;
R$^5$, R$^6$, R$^7$ and R$^8$ are independently H, F, Cl, Br, I, CH$_3$, CF$_3$, S(O)$_n$R$^{12}$ or CH$_2$CH$_3$, at least two of R$^5$, R$^6$, R$^7$, and R$^8$ being H;
R$^9$ and R$^{9A}$ are independently H or alkyl of 1 to 3 carbon atoms;
R$^{10}$ is OH, OCH$_3$, OCH$_2$CH$_3$, NH$_2$, NHCH$_3$ or N(CH$_3$)$_2$;
R$^{11}$ is (CH$_2$)$_{2-4}$NR$^9$R$^{9A}$;
R$^{12}$ is alkyl of 1–5 carbon atoms optionally substituted with one or more of F, Cl and Br;
W, Y and Z are independently H, F, Cl, Br, alkyl of 1–5 carbon atoms, NO$_2$, alkoxy of 1–5 carbon atoms, alkylthio of 1–5 carbon atoms, OH, CF$_3$ or NH$_2$;
m is 0 or 1;
n is 0 or 1; and
q is 0, 1 or 2; or
a pharmaceutically suitable salt thereof; with the following provisos:
(1) R$^5$, R$^6$ and R$^7$ cannot all be H;
(2) when R$^4$ is CO$_2$CH$_2$CH$_2$N(CH$_3$)$_2$, R$^6$ is CH$_2$CH$_3$, or R$^7$ is Cl, R$^1$ cannot be cyclohexyl; and
(3) when R$^1$ is cyclohexyl and R$^3$ is H, R$^6$ must be Cl or F, but R$^6$ and R$^8$ cannot both be Cl.

SUMMARY OF THE INVENTION

According to the present invention there are provided quinazoline-4-carboxylic acids having the formula:

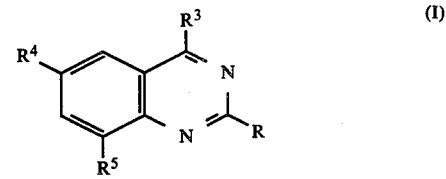

(I)

wherein
R is

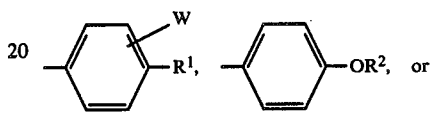

R$^1$ is alkyl of 5–12 carbon atoms, cycloalkyl of 3–7 carbon atoms, cycloalkyl alkyl of 4–12 carbon atoms, cycloalkenyl of 5–7 carbon atoms,

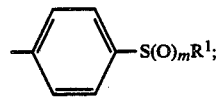

with the proviso that when R is

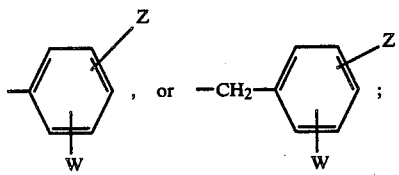

then R$^1$ can be in addition alkyl of 3–4 carbon atoms;
m is 0 or 1;
R$^2$ is

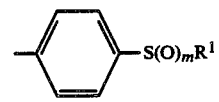

W and Z are independently H, F, Cl, Br, alkyl of 1–5 carbon atoms, NO$_2$, alkoxy of 1–5 carbon atoms, OH, CF$_3$, or NH$_2$;
R$^3$ is COOH, or COOR$^6$;
R$^4$ and R$^5$ are independently H, halogen, CF$_3$, or alkyl of 1 or 2 carbon atoms;
R$^6$ is

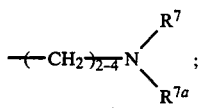

$R^7$ and $R^{7a}$ are independently H or alkyl of 1–3 carbon atoms;

or a pharmaceutically suitable salt thereof.

Preferred are the compounds of Formula (I) where:

(a) R is

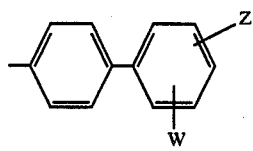

where W and Z are as defined above; or (b) $R^3$ is COOH or a salt thereof; or (c) $R^4$ and $R^5$ are independently H or halogen.

Specifically preferred for their antitumor activity are:

(a) 2-(1,1′-Biphenyl-4-yl)-6-fluoro-4-quinazoline carboxylic acid, sodium salt.

(b) 2-(1,1′-Biphenyl-4-yl)-4-quinazoline carboxylic acid, sodium salt.

Also provided are a process for preparing compounds of this invention, and an antitumor pharmaceutical composition containing at least one of the aforesaid compounds and a method of inhibiting the growth of mammalian tumors by administering to a mammal a tumor-inhibiting amount of at least one of the aforesaid compounds.

Synthesis

The compounds of Formula (I) are prepared as shown in Scheme I by reacting the potassium salt of an appropriately substituted isatinic acid (Formula III, o-aminophenylglyoxylic acid) with a desired carboxylic acid chloride to form a N-acylated isatinic acid (IV). The potassium salt of the isatinic acid is prepared according to the procedures described by G. J. Stefanovi, L. J. Lorenc and M. L. J. Mihailovi, *Rec. Trav. Chim.*, 80 149 (1961). The requisite isatins (II) are prepared according to the procedure described by Marvel and Hiers (*Org. Syn. Coll. Vol. I*, 327), and by the synthetic methods outlined by F. D. Papp and the references given therein [*Adv. Heterocyclic Chem.* 18, 1 (1975)]. The acid chlorides are prepared from the corresponding carboxylic acids by methods well known to one skilled in the art.

SCHEME 1

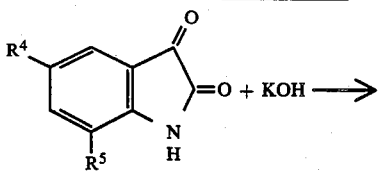

(II)

-continued
SCHEME 1

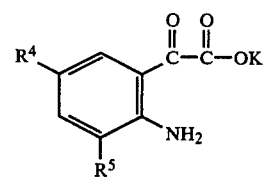

(III)

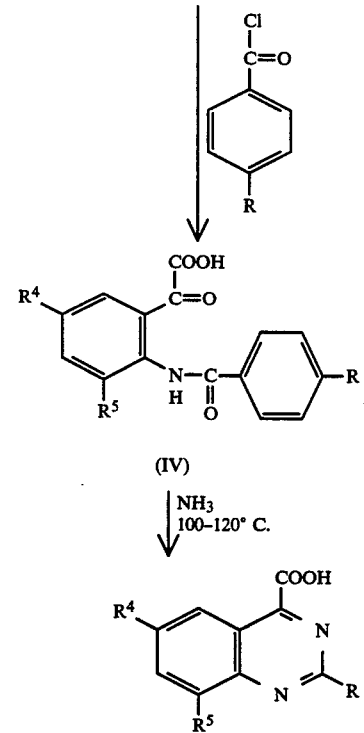

The condensation of the potassium salt of isatinic acid with a desired acid chloride is carried out in an anhydrous non-protic solvent, such as tetrahydrofuran, in the presence of an organic base, such as dimethylaminopyridine, or triethylamine. This procedure results in the desired N-acylated isatinic acid without the use of a large excess of the acid chloride (M. T. Bogert and F. P. Nabenhauer, *J. Am. Chem. Soc.*, 46, 1702 (1924)). The purified N-acylated isatinic acid is then allowed to react with ammonia, preferably in a solvent such as ethanol or methanol and the like and heated in a sealed tube under autogenous conditions at 100°–120° C. for a period of 6–8 hours resulting in cyclization to give the desired quinazolinecarboxylic acid (I).

This synthesis is general for quinazolines, including all those within the scope of this invention. When certain values of W and Z are desired, as will be apparent to one skilled in the art, a protected form of the functional group will be carried through the synthesis, to be deprotected to the desired functional group at a later stage.

SCHEME 2

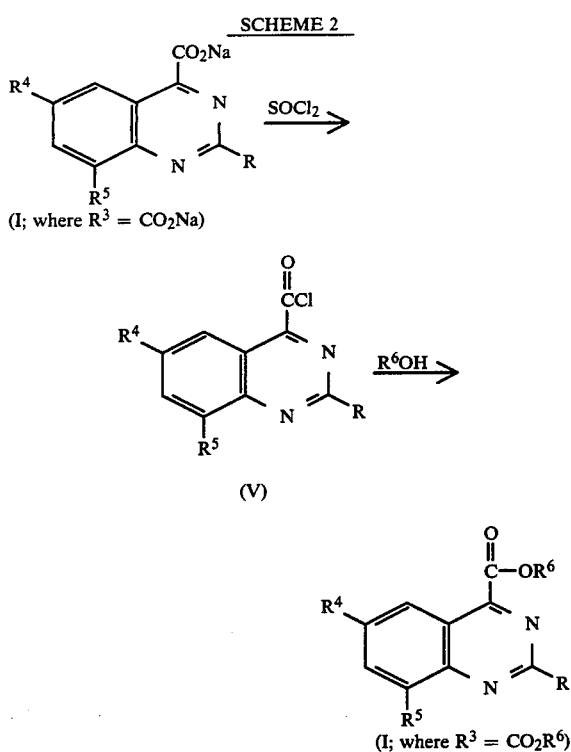

A salt of the carboxylic acid is prepared by dissolving the acid in a protic solvent such as ethanol, and then treating with a metal oxide or hydroxide such as sodium or potassium oxide or hydroxide or an amine such as 1-amino-2-butanol or lysine at a temperature in the range of about 0° C. to the boiling point of the solvent used. A salt of an amino group is prepared by dissolving the amine in a solvent such as ethyl ether and adding a mineral acid such as HCl.

A metal salt of a compound of Formula I (e.g., $R^3$=CO$_2$NA) can be converted to a corresponding ester in two steps. Conversion of the salt to an acid halide (V) is carried out first by treatment with a reagent such as SOCl$_2$ or oxalyl chloride in an inert solvent such as a hydrocarbon (benzene) at a temperature in the range of about 25° C. to the boiling point of the solvent used. This reaction is followed by the addition of an alcohol, $R^6$OH, in a solvent such as tetrahydrofuran at a temperature in the range of 10° C. to the boiling point of the solvent used, optionally in the presence of a base such as pyridine, triethylamine, or 4-dimethylaminopyridine to provide the ester (Scheme 2).

The preparation of compounds of the invention is further illustrated by the following Examples. Parts are by weight unless otherwise specified, and all temperatures are in degrees centigrade.

EXAMPLE 1

(1,1'-Biphenyl-4-yl)-4-quinazolinecarboxylic acid

Part (A)

2-1-[1,1'-Biphenyl-4-yl)carbonylamino]-α-oxobenzene acetic acid

Isatin was converted to the potassium salt of isatinic acid by the procedure described by G. J. Stefanovi, L. J. Lorenc and M. L. J. Mihailovi, *Rec. Trav. Chim.*, 80 149 (1961).

To a suspension of the potassium salt of isatinic acid (8.13 g, 0.04 moles) in tetrahydrofuran (150 ml) was added dimethylaminopyridine (1.3 g), followed by triethylamine (20 g, 0.2 mole). A solution of 4-biphenylcarbonyl chloride (16.3 g, 0.08 mole) in tetrahydrofuran (50 ml) was then added and the reaction mixture was stirred for a period of twenty hours. Water (10 ml) was added and the mixture stirred for an additional three hours. The suspended solids were filtered off and the filtrate evaporated to dryness in vacuo. The residue was then treated with 300 ml of water and the gum dissolved gradually. The aqueous solution was acidified with hydrochloric acid to pH 1. The precipitated solid was collected by filtration, thoroughly washed with water and air dried. Repeated trituration in boiling benzene removed the admixed 4-biphenylcarboxylic acid, and yielded the title compound (5.8 g), m.p. 200°-202°. Mass. Calcd. for $C_{21}H_{15}O_4N$: 346, found 346.

Part (B)

(1,1'-Biphenyl-4-yl)-4-quinazolinecarboxylic acid

A solution of 2-1-[(1,1'-biphenyl-4-yl)carbonylamino]-α-oxobenzene acetic acid (5 g) in ethanol (100 ml) was treated with anhydrous ammonia (25 g) and was then heated at 120° in a sealed tube under autogenous conditions for 6 hours. The cooled reaction mixture was then evaporated in vacuo, the solid residue suspended in 300 ml of water, acidified with acetic acid to pH 3-4, and stirred for one-half hour. The precipitated solids were collected, air dried, and recrystallized from ethanol to yield the title compound (3 g), m.p. 175°-176° (dec. with evolution of gas). Mass. Calcd. for $C_{21}H_{14}N_2O_2$: 326, found 326.

EXAMPLE 2

2-(1,1'-Biphenyl-4-yl)-6-fluoro-4-quinazolinecarboxylic acid

Part (A)

Potassium-(2-Amino-5-fluorophenyl)glyoxylate

A solution of 1N potassium hydroxide (100 ml) was gradually added to a suspension of 5-fluoroisatin (16.5 g, 0.1 mole) in water (100 ml). Periodically, the solution was gently warmed by immersion in a water bath maintained at 35°-40°. After most of the isatin dissolved, the insoluble residue was filtered off, and the clear filtrate evaporated to dryness in vacuo, at a bath temperature not exceeding 40°. Ethanol (400 ml) was added to the residue and the solids were triturated at room temperature. The potassium salt was collected by filtration and dried in a vacuum oven at room temperature for several days. (Yield 17 g).

Part (B)

2-[(1,1'-Biphenyl-4-yl)carbonylamino]-5-fluoro-α-oxobenzeneacetic acid

To a stirring suspension of the above described potassium salt (8.6 g, 0.04 mole) in tetrahydrofuran (100 ml) was added dimethylaminopyridine (1.4 g), followed by triethylamine (30 ml). A solution of 4-biphenylcarbonyl chloride (16.6 g, 0.08 mole) in tetrahydrofuran (50 ml) was then added and the reaction mixture was stirred for twenty hours. Water (10 ml) was added and the reaction mixture stirred for an additional four hours. The insoluble material was filtered off, and the filtrate evaporated to dryness. The residue was dissolved in 300 ml of water and the resulting aqueous solution was acidified to pH 1 by the addition of hydrochloric acid. The precipitated solids were collected, washed thoroughly with water and air dried. Repeated trituration from boiling benzene yielded 5 g of 2[(1,1'-biphenyl-4-yl)carbonylamino]-5-fluoro-α-oxobenzeneacetic acid which melted at 204°–206°. Mass. Calcd. for $C_{21}H_{14}FNO_4$: 363, found 363.

Part (C)

2-(1,1'-Biphenyl-4-yl)-6-fluoro-4-quinazolinecarboxylic acid

To 6 g of 2-[(1,1'-biphenyl-4-yl)carbonylamino]-5-fluoro-α-oxobenzeneacetic acid in ethanol (120 ml) was added anhydrous ammonia (27 g). The resulting mixture was heated in a sealed tube under autogenous conditions at 120° for six hours. The reaction mixture was cooled and the solvent and ammonia removed by evaporation in vacuo. The dry residue was suspended in water (200 ml) and the mixture was acidified with acetic acid to pH 3–4. The precipitated solids were collected, washed thoroughly with water and air dried. Recrystallization from ethanol afforded the title compound, m.p. 168°–169° (dec. with evolution of $CO_2$). Mass. Calcd. for $C_{21}H_{13}FN_2O_2$: 344, found 344.

EXAMPLE 3

2-(1,1'-Biphenyl-4-yl)-6-methyl-4-quinazolinecarboxylic acid

Using the procedure of Example 2, the title compound was prepared starting from 5-methyl isatin, m.p. 193°–196°.

The compounds of Examples 1–3 and other compounds which can be prepared following the procedures in Examples 1–3 are shown in Table I:

TABLE I

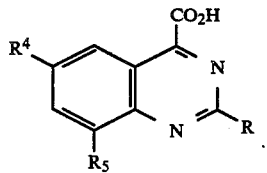

| Example | R | $R_4$ | $R_5$ | m.p. (°C.) |
|---|---|---|---|---|
| 1 | $4\text{-}C_6H_5C_6H_4$ | H | H | 175–176 (d) |
| 2 | $4\text{-}C_6H_5C_6H_4$ | F | H | 168–169 (d) |
| 3 | $4\text{-}C_6H_5C_6H_4$ | $CH_3$ | H | 193–196 (d) |
| 4 | $4\text{-}C_6H_5C_6H_4$ | $CH_3$ | F | |
| 5 | $4\text{-}(C_6H_5O)C_6H_4$ | F | H | |
| 6 | $4\text{-}(4\text{-}BrC_6H_4)C_6H_4$ | H | H | |
| 7 | $4\text{-}C_6H_5C_6H_4$ | $CH_3CH_2$ | H | |
| 8 | $4\text{-}C_6H_5CH_2OC_6H_4$ | F | H | |
| 9 | $4\text{-}C_6H_5C_6H_4$ | Cl | H | |
| 10 | $4\text{-}C_6H_5SC_6H_4$ | $CH_3$ | H | |
| 11 | $4\text{-}(4\text{-}FC_6H_4)C_6H_4$ | F | H | |
| 12 | $4\text{-}(4\text{-}CH_3OC_6H_4)C_6H_4$ | $CH_3$ | H | |
| 13 | $4\text{-}C_6H_5S(O)C_6H_4$ | H | H | |
| 14 | $4\text{-}C_6H_5C_6H_4$ | Br | Br | |
| 15 | $4\text{-}C_6H_5CH_2SC_6H_4$ | H | H | |
| 16 | $4\text{-}C_6H_5C_6H_4$ | $CF_3$ | H | |
| 17 | $4\text{-}(C_6H_5O)C_6H_4$ | $CF_3$ | H | |
| 18 | $4\text{-}(4\text{-}ClC_6H_4O)C_6H_4$ | F | H | |

TABLE I-continued

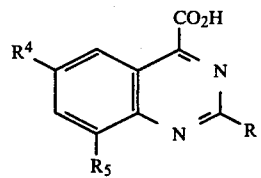

| Example | R | $R_4$ | $R_5$ | m.p. (°C.) |
|---|---|---|---|---|
| 19 | $4\text{-}\underline{c}\text{-}C_6H_{11}C_6H_4$ | H | H | |
| 20 | $4\text{-}\underline{c}\text{-}C_6H_{11}C_6H_4$ | F | H | 166–168 (d) |
| 21 | $4\text{-}(3\text{-}ClC_6H_4)C_6H_4$ | $CH_3$ | H | |
| 22 | $4\text{-}(2\text{-}FC_6H_4)C_6H_4$ | F | H | |
| 23 | $4\text{-}\underline{c}\text{-}C_5H_9C_6H_4$ | F | H | |
| 24 | $4\text{-}(4\text{-}FC_6H_4O)C_6H_4$ | $CH_3$ | H | |
| 25 | $4\text{-}(4\text{-}CF_3C_6H_4)C_6H_4$ | H | H | |
| 26 | $4\text{-}(4\text{-}BrC_6H_4)C_6H_4$ | Br | Br | |
| 27 | $4\text{-}(3\text{-}FC_6H_4)C_6H_4$ | F | H | |
| 28 | $4\text{-}(CH_3)_2CHSC_6H_4$ | F | H | |
| 29 | $4\text{-}(3\text{-}Cl,4\text{-}CH_3C_6H_3)C_6H_4$ | F | H | |
| 30 | $4\text{-}(4\text{-}(CH_3CH_2)C_6H_4)C_6H_4$ | $CH_3$ | H | |
| 31 | $4\text{-}C_6H_5CH_2C_6H_4$ | F | H | |

$\underline{c}\text{-}C_6H_{11}$ = cyclohexyl
$\underline{c}\text{-}C_5H_9$ = cyclopentyl

EXAMPLE 32

Sodium 2-(1,1'-Biphenyl-4-yl)quinazoline-4-carboxylate

The compound of Example 1 (1.63 g, 0.005 mole) was suspended in water (50 ml) and treated with 1N NaOH (5 ml). Ethanol was added until the suspension was in solution. The solution was filtered, and the ethanol and water were evaporated at reduced pressure to give 1.6 g of the sodium salt as a powder which was dried in a vacuum oven at room temperature, m.p. >360°.

EXAMPLE 33

Sodium 2-(1,1'-Biphenyl-4-yl)-6-fluoroquinazoline-4-carboxylate

The compound of Example 2 (2.41 g, 0.007 mole) was suspended in water (60 ml) and treated with a solution of 1N NaOH (7 ml) and enough ethanol was added to bring the mixture into solution. The solution was filtered to remove any insoluble material and the ethanol and water were evaporated at reduced pressure to give 2.3 g of the sodium salt as a white solid which was dried in a vacuum oven at room temperature, m.p. >360°.

EXAMPLE 34

Sodium 2-(1,1'-Biphenyl-4-yl)-6-methylquinazoline-4-carboxylate

The compound of Example 3 (2.4 g, 0.006 mole) was converted to the sodium salt (2.4 g, m.p. >360°) via the procedure described in Example 33.

The compounds of Examples 32–34, which have been prepared by the procedures given above, and other compounds which can be prepared using such procedures are listed in Table II.

TABLE II

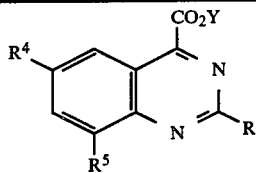

| Example | R | $R^4$ | $R^5$ | Y | m.p. (°C.) |
|---|---|---|---|---|---|
| 32 | $4\text{-}C_6H_5C_6H_4$ | H | H | Na | >360 |
| 33 | $4\text{-}C_6H_5C_6H_4$ | F | H | Na | >360 |
| 34 | $4\text{-}C_6H_5C_6H_4$ | $CH_3$ | H | Na | >360 |
| 35 | $4\text{-}C_6H_5C_6H_4$ | $CH_3$ | F | Na | |
| 36 | $4\text{-}(C_6H_5O)C_6H_4$ | F | H | Na | |
| 37 | $4\text{-}(4\text{-}BrC_6H_4)C_6H_4$ | H | H | Na | |
| 38 | $4\text{-}C_6H_5C_6H_4$ | $CH_3CH_2$ | H | Na | |
| 39 | $4\text{-}C_6H_5CH_2OC_6H_4$ | F | H | Na | |
| 40 | $4\text{-}C_6H_5C_6H_4$ | Cl | H | Na | |
| 41 | $4\text{-}C_6H_5SC_6H_4$ | $CH_3$ | H | Na | |
| 42 | $4\text{-}(4\text{-}FC_6H_4)C_6H_4$ | F | H | Na | |
| 43 | $4\text{-}(4\text{-}CH_3OC_6H_4)C_6H_4$ | $CH_3$ | H | Na | |
| 44 | $4\text{-}C_6H_5S(O)C_6H_4$ | H | H | Na | |
| 45 | $4\text{-}C_6H_5C_6H_4$ | Br | Br | Na | |
| 46 | $4\text{-}C_6H_5CH_2SC_6H_4$ | H | H | Na | |
| 47 | $4\text{-}C_6H_5C_6H_4$ | $CF_3$ | H | Na | |
| 48 | $4\text{-}(C_6H_5O)C_6H_4$ | $CF_3$ | H | Na | |
| 49 | $4\text{-}(4\text{-}ClC_6H_4O)C_6H_4$ | F | H | Na | |
| 50 | $4\text{-}\underline{c}\text{-}C_6H_{11}C_6H_4$ | H | H | Na | |
| 51 | $4\text{-}\underline{c}\text{-}C_6H_{11}C_6H_4$ | F | H | Na | >360 |
| 52 | $4\text{-}(3\text{-}ClC_6H_4)C_6H_4$ | $CH_3$ | H | Na | |
| 53 | $4\text{-}(2\text{-}FC_6H_4)C_6H_4$ | F | H | Na | |
| 54 | $4\text{-}\underline{c}\text{-}C_5H_9C_6H_4$ | F | H | Na | |
| 55 | $4\text{-}(4\text{-}FC_6H_4O)C_6H_4$ | $CH_3$ | H | Na | |
| 56 | $4\text{-}(4\text{-}CF_3C_6H_4)C_6H_4$ | H | H | Na | |
| 57 | $4\text{-}(4\text{-}BrC_6H_4)C_6H_4$ | Br | Br | Na | |
| 58 | $4\text{-}(3\text{-}FC_6H_4)C_6H_4$ | F | H | Na | |
| 59 | $4\text{-}(CH_3)_2CHSC_6H_4$ | F | H | Na | |
| 60 | $4\text{-}(3\text{-}Cl,4\text{-}CH_3C_6H_3)C_6H_4$ | F | H | Na | |
| 61 | $4\text{-}(4\text{-}(CH_3CH_2)C_6H_4)C_6H_4$ | $CH_3$ | H | Na | |
| 62 | $4\text{-}C_6H_5CH_2C_6H_4$ | F | H | Na | |
| 63 | $4\text{-}\underline{n}\text{-}C_6H_{13}C_6H_4$ | H | H | Na | |
| 64 | $4\text{-}C_6H_5C_6H_4$ | H | H | K | |
| 65 | $4\text{-}C_6H_5C_6H_4$ | F | H | K | |
| 66 | $4\text{-}C_6H_5C_6H_4$ | $CH_3$ | H | K | |
| 67 | $4\text{-}(4\text{-}FC_6H_4)C_6H_4$ | H | H | K | |
| 68 | $4\text{-}C_6H_5C_6H_4$ | H | H | lysine | |
| 69 | $4\text{-}(4\text{-}BrC_6H_4)C_6H_4$ | F | H | lysine | |
| 70 | $4\text{-}C_6H_5C_6H_4$ | $CH_3$ | H | 1-amino-2-butanol | |
| 71 | $4\text{-}C_6H_5C_6H_4$ | F | H | $(CH_2)_2N(CH_3)_2$ | |

$\underline{c}\text{-}C_6H_{11}$ = cyclohexyl
$\underline{c}\text{-}C_5H_9$ = cyclopentyl

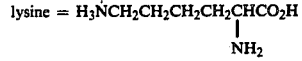

lysine = $H_3\overset{+}{N}CH_2CH_2CH_2CH_2CHCO_2H$
              |
              $NH_2$

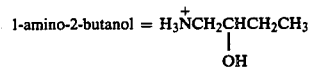

1-amino-2-butanol = $H_3\overset{+}{N}CH_2CHCH_2CH_3$
                        |
                        OH

Utility

The efficacy of the compounds of this invention against the transplanted mouse tumor was evaluated in a test system currently in use at the National Cancer Institute for the detection and assessment of anticancer activity. Most clinically effective drugs exhibit activity in this test and the test has a good record of predicting clinical efficacy [Goldin, A., Venditti, J. M., MacDonald, J. S., Muggia, F. M., Henney, J. E. and V. T. Devita, Jr., *Europ. J. Cancer,* 17, 129–142, (1981); Venditti, J. M., *Seminars in Oncology,* 8 (4) (1981); Goldin, A. and J. M. Venditti, in *Recent Results in Cancer Research,* 70, S. K. Carter and Y. Sakurai, Eds., Springer-Verlag, Berlin/Heidelberg, 1980].

Lymphoid Leukemia L1210

The animals used in this test were $CDF_1$ mice, all weighing a minimum of 17 g and all within a 4 g weight range at the start of the test. The test group consisted of six mice. The tumor was implanted in each of the test mice by the intraperitoneal injection of 0.1 ml of diluted ascitic fluid containing $10^5$ cells drawn from a mouse with L1210 leukemia. The test compounds were suspended in 0.25% Methocel ®/2% Tween ®80 or saline and injected intraperitoneally, at various doses, once daily for nine consecutive days starting on day one relative to the day of tumor inoculation (day 0). The control mice received injections of saline or 0.25% Methocel ®/2% Tween ®80 vehicle only. The mice were weighed and survivors were recorded on a regular basis for 30 days. The mean survival time and the ratio of the mean survival time for the treated (T) and control (C) mice was calculated. The mean survival time of the non-treated tumored mice ranged from 7-9 days. Drug effectiveness was assessed on the basis of the survival time. Results were expressed as a percentage of the control survival time (Mean Survival Time: T/C×100%). The criterion for effectiveness was determined by: T/C×100≧125 percent.

Results of tests with compounds of this invention are shown in Table III. The data indicate that the compounds of the invention are effective against the L1210 leukemia in mice.

TABLE III

| Example No. | L1210 Leukemia (dose in mg/kg) % T/C |
|---|---|
| 1 | (200)164 |
| 2 | (100)177 |
| 3 | (200)156 |
| 20 | (100)149 |
| 32 | (100)169 |
| 33 | (50)165 |
| 34 | (100)129 |
| 51 | (50)104* |

*should be active with more frequent dosing

Dosage Forms

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms, kind of concurrent treatment, frequency of treatment, and the effect desired. Usually a daily dosage of active ingredient can be about 5 to 400 milligrams per kilogram of body weight. Ordinarily 10 to 200, and preferably 50 to 200 milligrams per kilogram per day given in single doses or divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A quinazoline-4-carboxylic acid having the formula:

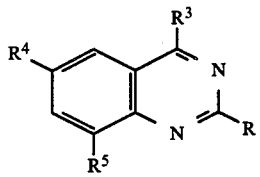

wherein
R is

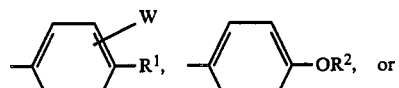

$R^1$ is alkyl of 5-12 carbon atoms, cycloalkyl of 3-7 carbon atoms, cycloalkyl alkyl of 4-12 carbon atoms, cycloalkenyl of 5-7 carbon atoms,

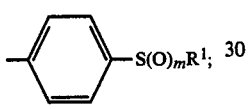

with the proviso that when R is

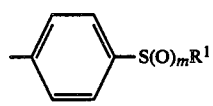

then $R^1$ can be in addition alkyl of 3-4 carbon atoms;
m is 0 or 1;
$R^2$ is

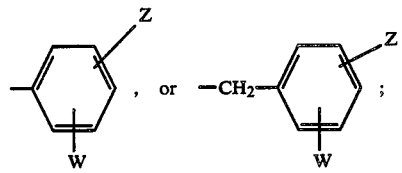

W and Z are independently H, F, Cl, Br, alkyl of 1-5 carbon atoms, $NO_2$, alkoxy of 1-5 carbon atoms, OH, $CF_3$, or $NH_2$;

$R^3$ is COOH, or $COOR^6$;
$R^4$ and $R^5$ are independently H, halogen, $CF_3$, or alkyl of 1 or 2 carbon atoms;
$R^6$ is

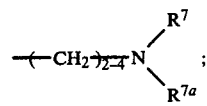

$R^7$ and $R^{7a}$ are independently H or alkyl of 1-3 carbon atoms;
or a pharmaceutically suitable salt thereof.

2. A compound of claim 1 wherein R is

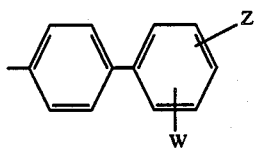

where W and Z are as defined in claim 1.

3. A compound of claim 1 wherein $R^3$ is COOH or a salt thereof.

4. A compound of claim 1 wherein $R^4$ and $R^5$ are independently H or Halogen.

5. A compound of claim 1 wherein
(a) R is

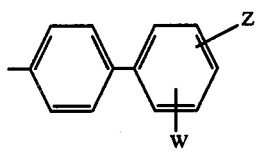

where W and Z are as defined in claim 1;
(b) $R^3$ is COOH or a salt thereof; and
(c) $R^4$ and $R^5$ are independently H or halogen.

6. The compound of claim 1 which is 2-(1,1'-biphenyl-4-yl)-6-fluoro-4-quinazoline carboxylic acid, sodium salt.

7. The compound of claim 1 which is 2-(1,1-biphenyl-4-yl)-4-quinazoline carboxylic acid, sodium salt.

8. A pharmaceutical composition consisting essentially of a suitable pharmaceutical carrier and at least one compound of claim 1.

9. A pharmaceutical composition consisting essentially of a suitable pharmaceutical carrier and at least one compound of claim 2.

10. A pharmaceutical composition consisting essentially of a suitable pharmaceutical carrier and at least one compound of claim 3.

11. A pharmaceutical composition consisting essentially of a suitable pharmaceutical carrier and at least one compound of claim 4.

12. A pharmaceutical composition consisting essentially of a suitable pharmaceutical carrier and at least one compound of claim 5.

13. A pharmaceutical composition consisting essentially of a suitable pharmaceutical carrier and the compound of claim 6.

14. A pharmaceutical composition consisting essentially of a suitable pharmaceutical carrier and the compound of claim 7.

15. A method of treating lymphoid leukemia in a mammal which comprises administering to a mammal an effective amount of at least one compound of claim 1.

16. A method of treating lymphoid leukemia in a mammal which comprises administering to a mammal an effective amount of at least one compound of claim 2.

17. A method of treating lymphoid leukemia in a mammal which comprises administering to a mammal an effective amount of at least one compound of claim 3.

18. A method of treating lymphoid leukemia in a mammal which comprises administering to a mammal an effective amount of at least one compound of claim 4.

19. A method of treating lymphoid leukemia in a mammal which comprises administering to a mammal an effective amount of at least one compound of claim 5.

20. A method of treating lymphoid leukemia in a mammal which comprises administering to a mammal an effective amount of at least one compound of claim 6.

21. A method of treating lymphoid leukemia in a mammal which comprises administering to a mammal an effective amount of at least one compound of claim 7.

* * * * *